United States Patent [19]

Childs et al.

[11] Patent Number: 5,783,399
[45] Date of Patent: Jul. 21, 1998

[54] CHEMILUMINESCENT ASSAY METHODS AND DEVICES FOR DETECTING TARGET ANALYTES

[75] Inventors: Mary Ann Childs; Gregory K. Shipman, both of Baltimore, Md.; William P. Trainor, Hillsboro Beach, Fla.; Erick Gray, Columbia; David Bernstein, Eldersburg, both of Md.

[73] Assignee: Universal Healthwatch, Inc., Columbia, Md.

[21] Appl. No.: 560,094

[22] Filed: Nov. 17, 1995

[51] Int. Cl.$^6$ .................. G01N 33/53; G01N 33/554; C12Q 1/00; C12Q 1/02
[52] U.S. Cl. .................. 435/7.2; 435/7.32; 435/8; 435/4; 435/29; 435/30; 435/34; 435/16; 435/18; 435/968; 435/283.1; 435/288.3; 435/288.7; 436/172; 422/50; 422/52
[58] Field of Search .................. 435/7.2, 7.32, 435/8, 4, 29, 30, 34, 283.1, 288.3, 288.7, 968, 16, 18; 422/50, 52, 68.1; 436/172

[56] References Cited

U.S. PATENT DOCUMENTS

| | | | |
|---|---|---|---|
| 4,385,113 | 5/1983 | Chapelle et al. | 435/8 |
| 4,396,579 | 8/1983 | Schreoder et al. | 422/52 |
| 4,863,689 | 9/1989 | Leong et al. | 422/52 |
| 5,366,867 | 11/1994 | Kawakami et al. | 435/8 |

OTHER PUBLICATIONS

DeLuca, M., et al. "Factors Affecting the Kinetics Of Light Emission From Crude and Purified Firefly Luciferase," *Anallytical Biochem.* 95:194–98 (1979) Month not available.

*Primary Examiner*—Louise Leary
*Attorney, Agent, or Firm*—Foley & Lardner

[57] ABSTRACT

A method which utilize chemiluminescence for analyte detection and the detection of bacteria on surfaces. The method uses a device comprising a sampling portion made of a first adsorbent material, a container, and a second adsorbent material located within the container. The sampling portion collects analytes from a test sample which includes a surface or volume of a liquid. The second adsorbent material holds one or more chemiluminescent components including luciferase enzyme and cofactors in a dry state. In a preferred embodiment, the sampling portion is swabbed over a suspected contaminated surface. A bacteriolytic solution is then added to the adsorbent and releases ATP from any bacteria present. The ATP diffuses into the second adsorbent and mixes with the reagents therein to produce detectable light.

16 Claims, 2 Drawing Sheets

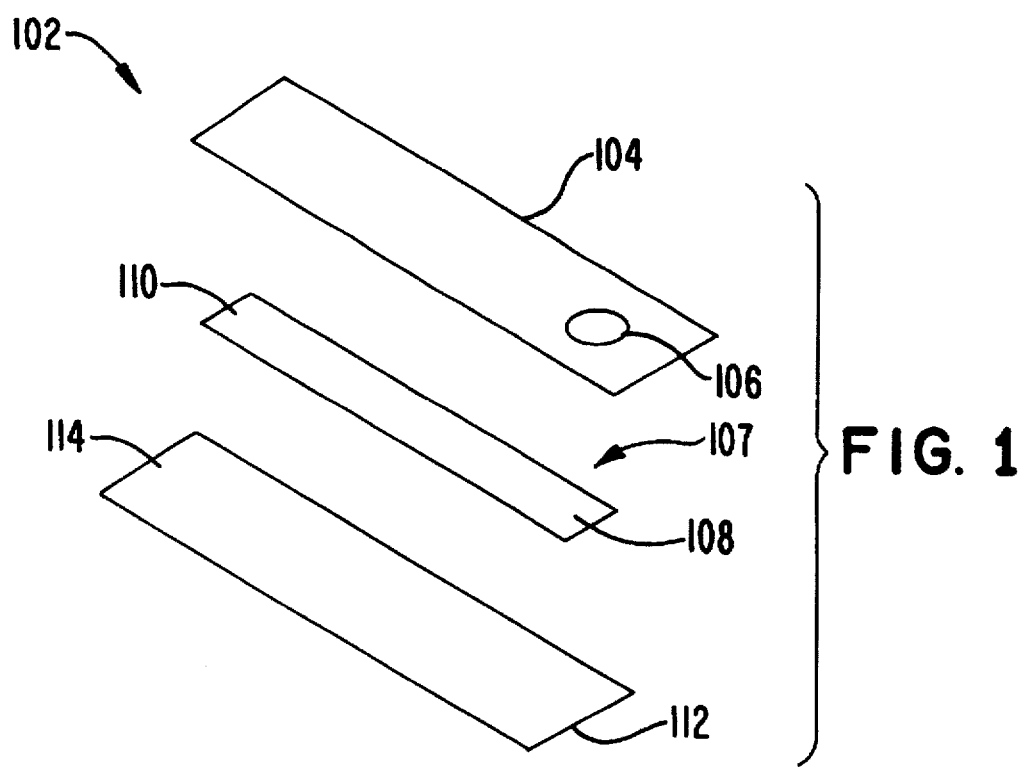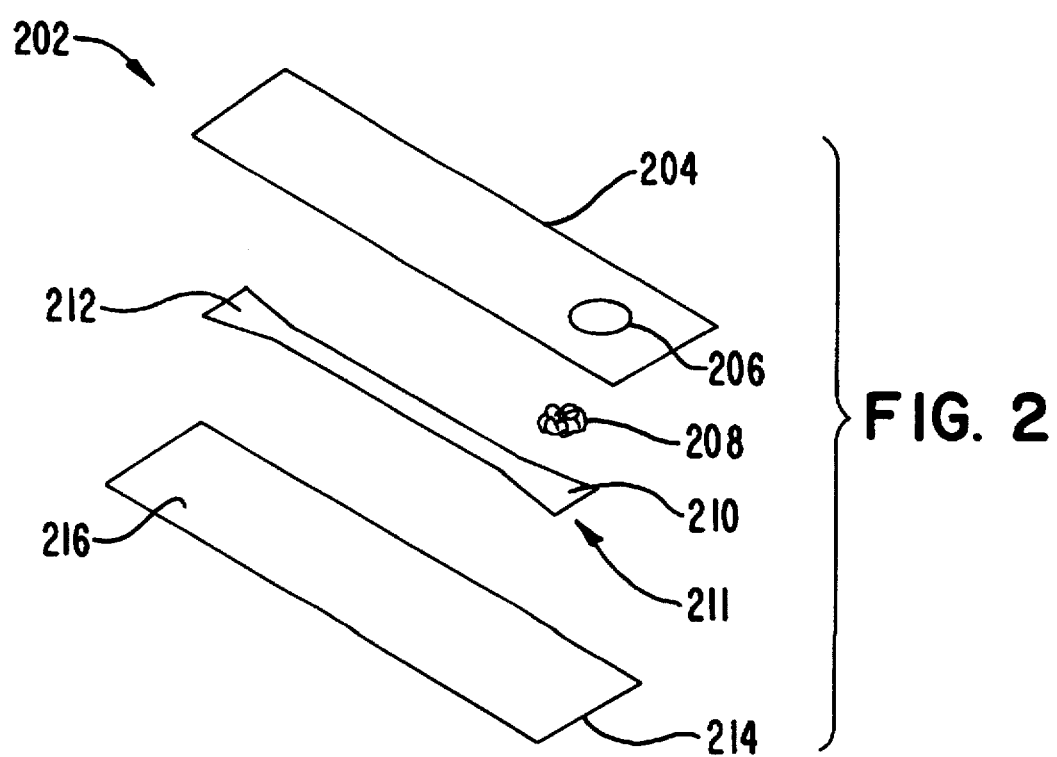

CHEMILUMINESCENT ASSAY METHODS AND DEVICES FOR DETECTING TARGET ANALYTES

FIELD OF THE INVENTION

The present invention relates generally to chemiluminescent assay methods and devices for detecting target analytes. In a preferred embodiment, the present invention relates to chemiluminescent assay methods and devices for detecting bacteria on contaminated surfaces.

BACKGROUND OF THE INVENTION

In the course of food processing, food becomes contaminated with bacteria and can spoil. If food is contaminated with pathogenic bacteria or its toxic products and then is ingested without proper cooking, human food poisoning can occur. The ability to reduce bacterial contamination of food is of major importance in improving food safety.

Standard culture plate methods for monitoring surfaces for bacterial contamination require a sterile sample collection device (generally a swab or sponge) and suitable culture media which, after inoculation, must be incubated at an appropriate controlled temperature for a minimum of several hours or days.

Unfortunately prior art methods for detecting bacterial contamination are too cumbersome and time consuming for immediate use by untrained workers. In particular, rapid bacteria tests are needed in slaughterhouses and food handling establishments. In these locations one must rapidly determine whether additional cleaning methods are required or whether proper safety procedures have been followed. Bacteria measurements would be a useful component of a "hazards and critical control points program" (HCCP) to monitor and control bacterial contamination. Unfortunately this is often not possible because present methods require several hours or even days by trained laboratory technicians.

One strategy to overcome these shortcomings has been the use of chemiluminescence detection methods to increase sensitivity (and thus decrease time) of the analytical method. One such chemiluminescence method measures adenosine triphosphate (ATP) to indirectly measure bacteria.

ATP detection is a reliable means to detect bacteria because all bacteria contain some ATP. Chemical bond energy from ATP is utilized in the chemiluminescent reaction that occurs in the tails of the firefly Photinus. The mechanism of this chemiluminescence reaction has been well characterized (DeLuca, M., et al, 1979 Anal. Biochem. 95:194–198). The components of this reaction can be isolated free of ATP and subsequently used to detect ATP in other sources by a reaction that begins with formation of an enzyme bound luciferyl-adenylate complex and free inorganic pyrophosphate and ends with a rapid reaction of this complex with molecular oxygen to produce light, $CO_2$ and AMP.

The traditional method for measuring light has been by photon counting with a photomultiplier tube. Photographic film has also been used. For example, U.S. Pat. No. 4,396,579 describes use of photographic film to monitor chemiluminescent reactions. This patent discloses a light detection device inside a closure which admits a cannula whereby fluid is introduced into a compartment. A drawback of the described device is that it is complex and requires the addition of fluid in the dark.

Luciferin-luciferase reactions of the firefly have been used for detecting a threshold level of microorganisms as described in U.S. Pat. No. 4,385,113 and 5,366,867. These reported methods, however, suffer a number of deficiencies. Lyophilized luciferase-luciferin reagent is unstable at room temperature during long term storage and is unstable after liquid reconstitution over short time intervals. Additionally, after reconstitution, solutions of this reagent display significant emission of light in the absence of ATP. This background decreases detection sensitivity and persists for several minutes to an hour.

The reagent instability problem was partly addressed by drying luciferin-luciferase reagents separately onto plastic surfaces. However, this solution to the problem requires the transfer of microorganisms from a collection device to a plastic surface. This transfer can occur by adding a solution to the collection device followed by transfer of the solution to a plastic surface that contains luciferase-luciferin reagents. This increase in complexity means that the user of the device must be trained in its use.

Unfortunately, this solution to the instability problem lowers sensitivity of the detection method. This solution creates a new problem of incomplete transfer of ATP from the collection device to a separate plastic surface that contains the luciferase-luciferin reagent. Furthermore, this solution introduces a new variable of time between the transfer and the light emission measurement.

Adding reagent at timed intervals causes a further problem because the light emission kinetics become shorter as the light intensity decreases.

The twin problems of timing and reagent instability also plague other chemiluminescence chemistries that have been developed to detect target analytes. For example, U.S. Pat. No. 4,396,579 (Luminescence detection device, Schroeder and Vogelhut) describes a complicated and expensive automated machine that was designed to add chemiluminescent reagent at fixed time intervals in order to overcome the problem of light emission kinetics. This machine was unusually complex because of the timing problem and because of the instability of reagents used with it.

Thus, there is a need for an assay which utilizes the high sensitivity and speed of chemiluminescence detection but which does not include the above mentioned problems of complexity, timing, reagent instability and high background light emission.

SUMMARY OF THE INVENTION

Accordingly, it is an object of the invention to eliminate or reduce the complexity of manually measuring and timing reagent additions required for the detection of target analytes.

A second object of the invention is to provide enhanced stability for chemiluminescent reagent(s) used in detection of target analytes.

A further object of the invention is to incorporate a light detection means into an assay device and to allow rapid measurement of target analytes at a sample site.

In accomplishing these and other objectives, one aspect of this invention provides a device for conducting a chemiluminescent assay. The device comprises a container, and a sampling portion comprising a first adsorbent material associated with the container. A second adsorbent material is located within the container and in the proximity of or in contact with the first adsorbent material. The second adsorbent material comprises at least one reagent portion into which one or more chemiluminescent reagents have been dried. The device has a light-permeable portion that permits light generated by a chemiluminescent reaction within the container to exit the container.

The device of the present invention eliminates or reduces much of the complexity associated with prior art assay methods and, as a result, decreases the cost and training requirements for detecting target analytes.

In a preferred embodiment, the device of this invention includes a film such as self-developing photographic film. This feature facilitates convenient readout and monitoring.

In accordance with another aspect of this invention, there is provided a convenient method for performing an assay for a target analyte. In this method, the sampling portion of the above-mentioned device is made to contact a sample, for example, by wiping the sampling portion over a surface suspected of containing the target analyte. A carrier liquid is then added to the sampling area, which liquid transports target analyte into the second adsorbent material. The carrier liquid also re-wets chemiluminescence reaction components in the reagent portion positioned along the longitudinal axis of the second adsorbent material, and thus allows a chemiluminescence reaction to begin. The instability problem suffered by prior art methods is overcome by providing the chemiluminescent reagent in a dried state within the reagent portion and/or sampling portion.

In another preferred embodiment the method is used to rapidly detect bacteria on surfaces such as countertops and equipment used in meat or food production. In this method, high sensitivity is achieved by incorporating components of the luciferase chemiluminescence reaction in a dried form into at least one reagent portion. A bacteriolytic agent (e.g., a detergent) in the carrier liquid lyses bacteria that have been collected in the sampling portion. ATP liberated by lysis of bacteria then participates in a luciferase reaction to produce light. The advantage of rapid and sensitive detection of bacteria can be realized, for example, through sensitive light detection with a photomultiplier or high speed film that is physically part of the device container.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 is a top perspective exploded view of a device in accordance with this invention.

FIG. 2 is a top perspective exploded view of another device in accordance with this invention depicting the positioning of a fibrous adsorbent sample portion.

DETAILED DESCRIPTION OF THE PREFERRED EMBODIMENTS

Figure 3:
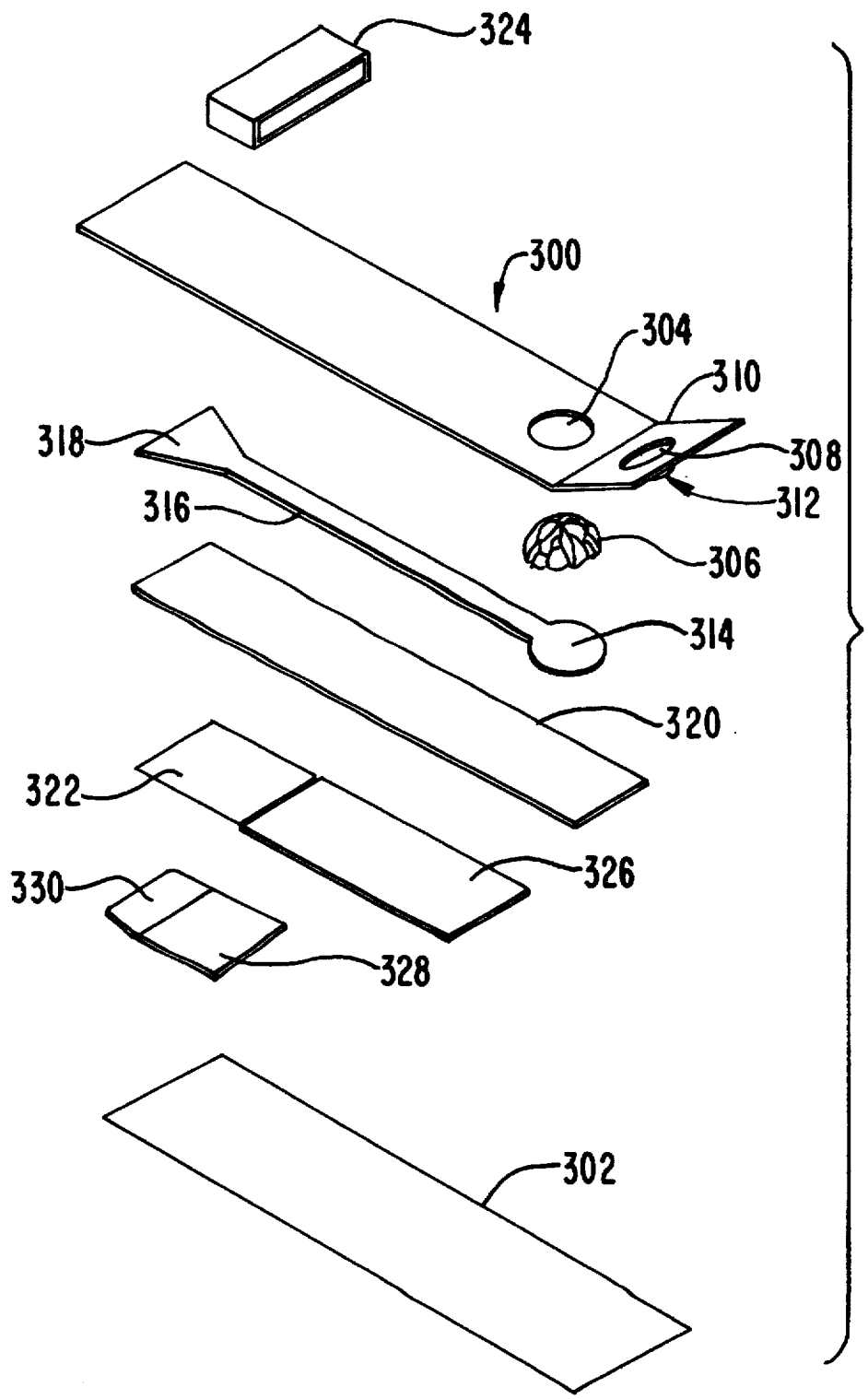
FIG. 3 is a top perspective exploded view of another device in accordance with this invention comprising a carrier liquid and a photographic film detection means.

The present inventors discovered that, for a chemiluminescence system, the luciferase enzyme and necessary cofactors could be dried onto a porous adsorbent material and subsequently reconstituted in an assay of the disclosed configuration for bacteria and other analytes. Moreover, the present inventors discovered that such reagents could be combined into a convenient device as disclosed herein that included a sampling portion and a second adsorbent material that permits flow along a longitudinal axis.

In its most basic form for the detection of analytes from surfaces and liquids or other areas where analytes can be found, the process of this invention comprises three steps: 1) contacting the surface, liquid, or other area suspected of containing the analyte by swabbing with or applying a liquid onto the sample portion; 2) applying a carrier liquid to the sample portion to wash target analyte from the sample portion into an adsorbent material comprising a reagent portion and, at the same time reconstitute dried reagent; and 3) subsequently detecting light produced by chemiluminescence in response to the presence of target analyte in a sample. It is noted that step 2 (application of a carrier liquid) may not be needed if the target analyte to be tested is in a liquid.

A wide range of target analytes can be detected by the invention. A target analyte as used herein, is a molecule such as a protein, cell metabolite or microorganism such as a prokaryotic cell, virus, microplasma or free living eukaryotic cell.

In fact, the sampling portion of the device can collect virtually any type of target analyte. The target analyte can be introduced to the sampling portion of the device, for example, by application of a fluid by means of, for example, an eye dropper or other dispenser, or by brief immersion of the device in a fluid or stream of fluid. Alternatively the target analyte can be introduced by physical contact such as by swabbing a suspected contaminated surface with the device.

In one preferred embodiment of the invention, suspect surfaces such as countertops, kitchen utensils and slaughterhouse machinery are tested for bacterial contamination by swabbing the suspect contaminated surface with the sampling portion of the device.

The sampling portion is comprised of an adsorbent material. The adsorbent material may be fibrous, such as glass fiber, cotton, dacron, or paper, and it may be porous, such as porous polyethylene or sintered glass.

The second adsorbent material may be fibrous, such as glass fiber, cotton, dacron, or paper and the like, and it may be porous, such as porous polyethylene or sintered glass and the like. The second adsorbent material may be the same as or different than the first adsorbent material. The first and second adsorbent materials can be distinct pieces of the same or different material, or they may be one piece of the same material, or they may be different materials joined together to forma a continuous material. In any event, the first adsorbent material of the sampling portion is in proximity to or in physical contact with a second adsorbent material such that fluid applied to the sampling portion will enter the second adsorbent material and diffuse into the reagent portion.

The second adsorbent material generally is thin, having a longitudinal axis that generally will be defined by the location of the sampling portion and the reagent portion. This second adsorbent material also generally will have an insubstantial thickness such that diffusion through the material primarily occurs along the direction of the longitudinal axis, one goal being to provide sufficient analyte for reaction with the reagents present. The material can be in various shapes including, for example, round, oval, rectangular, narrow in the middle and wider at each end, etc. The shape provides for diffusion and mixing of reagents and, advantageously, allows a substantial exposure of surface area to the light detection means. Those skilled in the art readily will recognize many useful materials, such as those used in chromatographic-type assays currently available.

The reagent portion often will be only part of a porous adsorbent strip as shown in the Figures. The reagent portion can contain one or more reagents for the chemiluminscent reaction, generally in dried form. Additionally, it can contain other reagents useful for the assay including, for example, the detergent or other bacteriolytic reagent necessary to extract ATP from bacteria. The reagents can be mixed together or placed sequentially along the longitudinal axis of the second adsorbent material so that the diffusing fluid contacts the reagents sequentially.

Detectible chemiluminescent light may be emitted within the reagent portion and/or may be emitted downstream of the reagent portion (where the chromatically moving reagents will move), once the reaction has become sufficient to generate detectable light. A satisfactory location on the adsorbent material for detecting the reaction will be easily determined and will depend upon such factors as the type and amounts of reagents, type of adsorbent material, etc.

A portion of the device is at least partially transparent to the light emitted by the chemiluminescent reaction. This can be achieved, for example, by using transparent plastic for the device although other means, such as windows or sonic welded transparent portions are suitable. Particularly suitable is the use of a transparent covering over a surface near the reagent portion of the second adsorbent material (or other satisfactory location for detecting light, as discussed above).

A wide variety of chemiluminescent chemistries can be used in the devices and methods of this invention. Acceptable chemiluminescence chemistries include, among others, the reaction of hydrogen peroxide with horseradish peroxidase labelled antibodies and luminol, enhanced horseradish peroxidase, reactions that include the use of diacylhydrazides, acridinium salts, dioxitanes, and bioluminescent reactions involving cofactors such as reduced nicotine adenine dinucleotide in the case of marine bacteria.

A particularly preferred chemiluminescent chemistry is the firefly ATP assay which utilizes luciferase and at least one cofactor to generate light from ATP that is present in a sample.

At least one chemiluminescent reaction reagent is present in a reagent portion of the second adsorbent material in a dry state. During preparation of the reagent portion a reagent may be conveniently applied to the second adsorbent material as a wet water solution and dried during manufacture or it may be applied in a dry form, such as a powder or suspension in a organic solvent or slurry. Other methods are known in the art and the preferred one is determined by characteristics of the reaction components.

Acceptable carrier liquids include, among others, buffer, buffer with detergent, water, blood and urine. Buffer solutions of TRIS, HEPES buffers at pH 7.0 to 9.0, and most preferably HEPES buffer at 7.8 with EDTA are preferred. EDTA is a preferred ingredient because ATP degrading enzymes require divalent metal cations for activity and EDTA chelates these.

In an optional embodiment, detergent is present in the sample portion or reagent portion, or elsewhere in the second adsorbent material. The detergent dissolves in fluid that is added to the device and it serve to open cells and liberate cell components.

An optional further use of the carrier liquid is to release one or more substances from microorganisms in the sample portion. In this embodiment the carrier liquid lyses any collected bacteria in the sampling portion and releases ATP from the bacteria into the solution for transport into the reagent portion. Detergent can be included in the carrier liquid for this purpose.

Several suitable detergents or combination of detergents are known to those skilled in the art and include, nonionic detergents such as Triton X-100, Tween 20, Nonidet P40, n-Undecyl Beta-D glucopyranoside, Zwitterionic detergents such as n-hexadecyl-N,N-dimethyl-3-ammonio-1-propanesulfonate, and cationic detergents such as alkyltrimethylammonium bromides, benzalkonium chloride, cetyldimethyl-ethylammonium bromide, dodecyltrimethylammonium bromide, and cetyltrimethylammonium bromide. The concentration of detergent solution varies for each type of detergent and can range from 0.1% to 6%, and preferably from 0.5% to 2.0%.

In an advantageous embodiment the carrier liquid is present in a reservoir that is present in the assay device. For example, the reservoir can be positioned on the device adjacent to a flexible area (e.g., hinge, or integral hinge). The flexible area permits the reservoir to be manipulated so that it is positioned proximate the sampling portion. In this way, after the sampling portion contacts the target analyte, the portion of the device containing the reservoir can be contorted or folded over so that the reservoir is positioned proximate (e.g., directly on top of) the sampling portion. The reservoir then can be broken (e.g. by finger pressure) so that its contents are released directly on the sample portion. In this embodiment, therefore, there is no need for additional, separate containers for reagents since all reagents are present in the test device.

The container itself should be constructed of liquid impermeable material, such as a plastic. The container can be made, for example, by molding a single piece of plastic into a shape that can house the adsorbent material of the sampling and reagent portions. Alternatively, the container can be constructed from multiple elements that are sealed to provide a liquid impermeable seal. The container optionally may have an opening to enhance the diffusive or chromatographic flow of liquid along the adsorbent material therein. Alternatively, an air pocket within the container can be provided for such purpose. The container need not completely surround the second adsorbent. The container can be open on one or more sides to expose the second adsorbent to air. It is preferable that the container is liquid impermeable where the container contacts the second adsorbent so that liquid does not adsorb into or pass through the container.

The step of detecting chemiluminescent light emitted from the container can be accomplished by a number of means known to those skilled in the art. Chemiluminescent light can be detected electronically by, for example, a photomultiplier, photo diode, photo fet or charge coupled device. The most preferred electronic light detector is a photomultiplier because of its sensitivity.

Chemiluminescent light also can be detected chemically, for example by the use of a film. Particularly preferred is high speed photographic film such as Polaroid #612 which has a speed equivalent to ASA 20,000. Those knowledgeable in the areas of films will appreciate many other types of suitable films.

The intensity of light emitted from the chemiluminescent reaction obeys an inverse square relationship to distance following Lambert's Law. Therefore, if a light detector is used, detection sensitivity may be enhanced by placing the detector close to a place where detectible light is emitted.

For light detection with electronic readout methods, the device may be inserted into a complementary-fitting dark chamber wherein a light detector is proximal to the test area and distal to the sampling area of the device. This latter means overcomes the complexity of some of the prior art in that no timed or measured reagent addition in the dark is required. This can improve the cost and convenience of the subject device and method.

Referring now to the Figures, several embodiments of this invention are provided.

FIG. 1 depicts a basic form of the sample-test device 102 in which the sample portion adsorbent material and second adsorbent material are combined as one material. The first element 104 comprises an impervious material such as a plastic film having an opening 106. The adsorbent material 107 has dried reagent along its longitudinal axis (e.g., dried luciferase reagent), which extends from sampling portion 108 to detection area 110. Light preferably is detected from detection area 110 although, if desired, light also can be detected from other parts of the device.

During operation, the sampling portion, which is the portion of adsorbent material 107 exposed through opening 106, is contacted with a sample suspected of containing the target analyte. Then, a carrier liquid (if necessary) is added to the sampling portion and carries with it any analyte as it diffuses along the adsorbent material 107, mixing any analyte present with the chemiluminescent reagent therein. The reaction mixture diffuses then into the detection area 110 where sufficient light is emitted for detection.

The third element 112 is comprised of an impervious material such as plastic film and is light permeable at least in region 114 directly below the detection area 110. Alternatively, the first element 104 could be light permeable above the detection area. The light permeable region 114 can, for example, be positioned close to a light detector. The adsorbent material 107 is thus sandwiched between plastic layers 104 and 112 which are sealed together, for example, by heat, adhesive, or physical means that retain the sides of the two elements clamped together.

FIG. 2 depicts another device in accordance with this invention 202 that comprises a sampling portion adsorbent material that is distinct from the second adsorbent material. The first element 204 comprises a liquid impervious material such as a plastic film having an opening 206. The sampling portion 208 is comprised of fibrous adsorbent material. The sampling portion 208 is positioned directly under opening 206 between the top impervious layer 204 and one end 210 of the second porous absorbent material 211. Second adsorbent material 211 is wider at each end of its longitudinal axis and narrow in its middle. Element 214 comprises a liquid impervious material which is light permeable, at least in the area 212 where chemiluminescent light will be emitted. Although not shown in the figure, one or more holes may be present in elements 204 and 214 near end 216 in order to facilitate the passage of fluid away from sampling portion 208.

FIG. 3 depicts another device in accordance with this invention that is useful for detecting the presence of bacteria. The device comprises separate sampling portion adsorbent and second adsorbent materials as shown in FIG. 2, but additionally comprises a carrier liquid (located in reservoir 308) and instant photographic film light detection means.

The first element 300 comprises a liquid impervious material such as a plastic film having an opening 304, a reservoir 308 with surface 312, and flexible area (e.g., hinge) 310. Sampling portion 306 is comprised of a first porous adsorbent material, and is positioned directly under opening 304 between the top impervious layer 300 and one end 314 of a second porous absorbent material 316 that is wider at each end of its longitudinal axis and narrower in its middle. Another element 320 comprises a liquid impervious material which is at least partially light permeable. Although not shown in the figure, one or more holes may be present in element 300 and 320 in order to facilitate the passage of fluid away from sampling portion 306.

The device of FIG. 3 also comprises negative film layer 322, compressing bar 324, developing gel container 326, and positive print film 328 with attached tab 330. These components allow detection of chemiluminescent light by instant photographic means.

In using the assembled device, finger pressure is placed on backing 302 in an area behind opening 304 through which exposed adsorbent of sample portion 306 is used, for example, to wipe the surface of a test area. After wiping, the portion of the device comprising carrier liquid reservoir 308 is folded over at flexible area 310. Pressure is applied to reservoir surface 312 which causes the reservoir to break and release the carrier liquid from the reservoir and into sample portion 306.

The carrier liquid comprises a bacteriolytic agent that releases ATP from any bacteria present in the sampling portion 306. The ATP diffuses through sampling portion 306 and into absorbent material 316 at point 314. The solution diffuses through the body of the adsorbent strip where it rehydrates dried chemiluminescent reagent present therein. Any ATP present in the carrier liquid reacts with the rehydrated chemiluminescent reagent present and light is detected at area 318.

Light from chemiluminescence passes through light-permeable element 320 and enters negative film layer 322. After appropriate incubation time for exposure of the film, compressing bar 324 is moved across the device from the direction of point 314 to detection area 318, and compresses developing gel container 326. This forces developing gel from the developing gel container 326 across the surface of negative film 322 and positive print film 328. After an appropriate development time, tab 330 is pulled and the positive print film is viewed to determine the presence or absence of the target analyte (bacteria).

The following example is presented by way of illustration and not by way of limitation.

EXAMPLE 1

A cellulose filter paper (Scientific Products Filter paper Grade #361) is cut into a strip 10 mm×35 mm. Luciferase-luciferin (Analytical Luminescence Systems) is reconstituted with a solution of 5% alpha-D-glucopyranosyl alpha-D-glucopyranoside in 0.05M dithiothreitol. Fifteen microliters of the Luciferase-luciferin solution are pipetted at approximately 15 mm from the distal end of the filter paper strip and dried in vacuo.

An adhesive coated plastic is cut into a 12.5 mm×40 mm strip. A 8.0 mm diameter hole is punched out at the proximal end of the strip. The perimeter of the hole is centrally located approximately 3.5 mm from the proximal end of the strip.

An adhesive coated translucent plastic strip is cut into a 12.5 mm×40 mm strip. With the adhesive side of the translucent plastic strip facing up, the filter paper strip is positioned wherein the edge of the distal end of the filter paper is 2.5 mm from the distal end of the translucent plastic strip and the proximal portion of the filter paper is 2.5 mm from the proximal end of the translucent strip. A plug of dacron fibers approximately 10 mm in diameter is centered close to but not extending beyond the edge of the proximal portion of the filter paper strip. The adhesive coated plastic strip with adhesive side facing downward is positioned directly over the translucent strip and oriented so that the punched hole is directly over the dacron plug. Pressure is applied to the device to seal the adhesive backings together.

An individual Polaroid film packet (#612 ISO 20,000) is cut down into a 12.5 mm×20 mm rectangle and glued to the proximal undersurface of the device, becoming an integral part of the device forming a dark chamber wherein the photographic film is adjacent to the test portion of the filter paper.

The device is held between the fingers with dacron side facing the surface to be monitored for bacteria. Finger pressure is applied on the back side of the device directly behind the sampling area, and the dacron sampling portion is used to wipe a defined area. One hundred and fifty microliters of an extraction buffer that contain 0.05M HEPES buffer pH 7.8 and 0.5% Cetyldimethylethylammonium bromide is added to the punched out hole containing the dacron sampling area. The extracted ATP, if present, diffuses across the porous filter, the luciferase-luciferin reagent dissolves, and light is emitted as the solution flows across the distal portion of the filter paper. A film is exposed to light emitted over a given period of time at the test area. After 2 minutes, the film is developed and peeled back from the device to reveal a white spot if positive, or no white spot if negative.

The above example is presented for purposes of clarity of understanding. It will be obvious that certain changes and modifications may be practiced within the scope of the appended claims.

What is claimed is:

1. A method of performing a chemiluminescent assay for a target analyte, comprising the steps of:
   A. providing a device comprising:
      i. a container that is substantially impermeable to liquid;
      ii. a sampling portion physically associated with said container, said sampling portion comprising an adsorbent material;
      iii. a second absorbent material located within said container, said second absorbent material having a longitudinal axis, said first and second absorbent materials being in proximity to or in physical contact with each other; and
      iv. at least one reagent portion that is positioned along said longitudinal axis of said second absorbent material, said reagent portion comprising a reagent that participates in a chemiluminescent reaction, wherein said container comprises a light-permeable portion that permits at least a portion of light generated from a chemiluminescent reaction within said container to pass to the outside of said container;
   B. contacting a test sample suspected of containing the target analyte with said sampling portion;
   C. introducing to said sampling portion at least one carrier liquid that transports target analyte from said sampling portion into said second adsorbent material; and
   D. detecting light produced within said container due to the presence of said target analyte in the sample during a chemiluminescent reaction in step c.

2. The method according to claim 1, wherein, after Step A, said sampling portion is contacted with a carrier liquid comprising a target analyte extraction reagent that extracts target analyte present in said sampling portion.

3. The method according to claim 2, wherein, said target analyte extraction reagent is present in said at least one carrier liquid.

4. The method according to claim 2, wherein, said target analyte is ATP.

5. The method according to claim 2, wherein said target analyte extractor reagent comprises a compound selected from the group consisting of cetyldimethylethylammonium bromide, Triton X-100, Tween 20, Nonidet P40 and n-hexadecyl-N,N-dimethyl-3-ammonio-1-propanesulfonate.

6. The method according to claim 1, wherein, Step C comprises detecting said light using an electronic instrument.

7. The method according to claim 1, wherein, Step C comprises detecting said light using a film.

8. The method according to claim 7, wherein said film is a self-developing photographic film.

9. A method of performing a chemiluminescent assay for bacteria, comprising the steps of:
   A. providing a device comprising:
      i. a container that is substantially impermeable to liquid;
      ii. a sampling portion physically associated with said container, said sampling portion comprising an adsorbent material;
      iii. a second absorbent material located within said container, said second adsorbent material having a longitudinal axis, said first and second adsorbent materials being in proximity to or in physical contact with each other; and
      iv. at least one reagent portion that is positioned along said longitudinal axis of said second adsorbent material, said reagent portion comprising a reagent that participates in a chemiluminescent reaction; wherein said container comprises a light-permeable portion that permits at least a portion of light generated from a chemiluminescent reaction within said container to pass to the outside of said container;
   B. wiping a test surface suspected of containing the bacteria with said sampling portion;
   B. contacting said sampling portion with a reagent that extracts ATP present in said sampling portion; and
   C. detecting light produced within said container due to the presence of said bacteria on the test surface during a chemiluminescent reaction in step b.

10. A method according to claim 9, wherein said reagent comprises a compound selected from the group consisting of cetyldimethyl-ethylammonium bromide, Triton X-100, Tween 20, Nonidet P40 and n-hexadecyl-N,N-dimethyl-3-ammonio-1-propanesulfonate.

11. A method according to claim 9, wherein, Step C comprises detecting said light using an electronic instrument.

12. A method according to claim 11, wherein, Step C comprises detecting said light using a film.

13. A method according to claim 12, wherein said film is a self-developing photographic film.

14. A method according to claim 9, wherein said device further comprises:

A. a reservoir comprising a carrier liquid, said carrier liquid comprising a bacteriolytic solution that extracts ATP from bacteria; and B. a flexible area adjacent to a reservoir which permits the reservoir to fold or bend such that it can be positioned proximate to the sampling portion; and wherein, Step B is carried out by bending the device at the flexible area so that the reservoir is positioned proximate to the sampling portion, and then breaking the reservoir so as to release carrier liquid into the sampling portion.

15. A method according to claim 14, wherein, Step C comprises detecting said light using a film.

16. A method according to claim 15, wherein said film is a self-developing photographic film.

* * * * *